May 16, 1972 W. H. DANIEL Plant Pat. 3,177
KENTUCKY BLUEGRASS (POA PRATENSIS)
Filed July 7, 1969
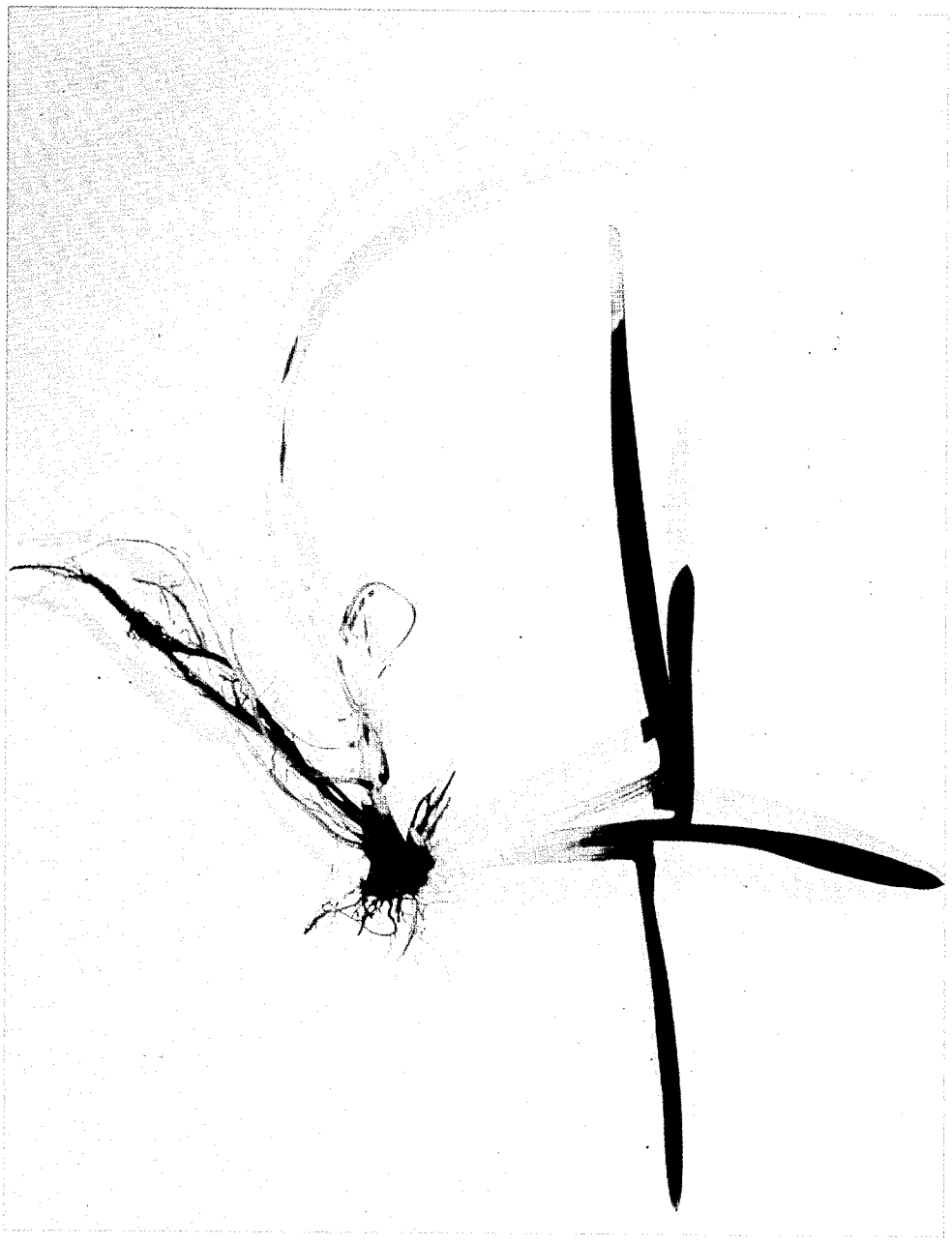
INVENTOR
WILLIAM H. DANIEL
BY: J Moslitt
ATTORNEY

United States Patent Office

Plant Pat. 3,177
Patented May 16, 1972

3,177

KENTUCKY BLUEGRASS (*POA PRATENSIS*)

William H. Daniel, West Lafayette, Ind., assignor to Purdue Research Foundation

Filed July 7, 1969, Ser. No. 839,734
Int. Cl. A01h *5/00*
U.S. Cl. Plt.—88 1 Claim

This invention relates to a new and distinct variety of Kentucky bluegrass, *Poa pratensis,* designated as AQ6, and found in the Purdue University nursery, West Lafayette, Indiana, in 1963.

As history, AQ6 is a resultant cross when clones of preferred turf types were paired adjacent in numerous combinations in a 1962 planting. Seed from Merion (mother) surrounded by Dwarf (male) after crossing under approved (overturned bag) technique was labeled cross AQ from which seedling 6 was observed as a new and different plant.

Increased vegetative parts of AQ6 clone showed dark green color (1.3 rating), medium spread (5.1 rating), excellent leafspot tolerance and desired low leaf characteristics. Seed from increase planted as Row 96 in greenhouse bench 5–1 in December 1964, gave uniform seedlings which showed early rhizome formation (averaged 25 when Windsor averaged 20), excellent powdery mildew resistance, and good shade tolerance. Seedlings were potted singly, then transplanted in June 1965 into field as spaced plants.

The leaves are wide (3–6 mm.), and short in length (6–8″) when some leaves are up to 20″ for some selections in total test in June 1967 measurements. The leaf angle is wide 60–80°, and leaf sheaths are thin with a heavy well-developed collar. Crowns or turf of spaced plants are open and thin as strong individual rhizomes emerge as individual tillers—not clusters.

The AQ6 seedhead is longer and lighter in color, and it has a narrower, thinner profile compared to Dwarf. Seedhead height was in lower ⅓ of all experimental 15″ in Lafayette (range in test of 3600 plants of 100 sources was 6–30″). When irrigated, fertilized and all spaced plants given equal treatment seed production is improved over Merion, S–2 and Dwarf. Near Spokane, Wash. on 4 rows of each in 1968, Dwarf produced 130 lbs. when AQ6 produced 214 lbs. At Purdue in field 9A3 in 1966, AQ6 rated 3—good for quantity of seed, and highest of the 4 lines in Sodco in height when mature, being 20″.

As a plant AQ6 shows excellent stem rust resistance (rating of 1.6) based on 39 individual plants in Purdue field 9A3 in 1966 (rating 1 best, 9 worst) which is different from and superior to Merion (mother) and Dwarf (father) (both get stem rust) and is also additive to the qualities of of Dwarf, 16–BB56, and RI–10, each are described in co-pending U.S. plant patent applications Ser. Nos. 839,731, 839,733 and 839,734, respectively.

Comparison of AQ6, with Dwarf, 16–BB56 and RI–10 are as follows:

| | Dwarf | AQ6 | 16-BB56 | RI-10 |
|---|---|---|---|---|
| Plants, number of | 285 | 39 | 35 | 200 |
| Years when data was taken | 1965-68 | 1966 | 1966-68 | 1965-68 |

| Character | Dwarf | AQ6 | 16-BB56 | RI-10 | Comment |
|---|---|---|---|---|---|
| Leaf height, inches | 7.2 | 5.2 | 8.5 | 6.6 | Low. |
| Spread rating, 1 most | 5.9 | 5.1 | 4.7 | 5.8 | Only medium. |
| Color-rating, 1 greenest | 3.3 | 1.3 | 3.7 | 3.2 | Dark green. |
| Stripe smut resistance 1 best | 1 | 1 | 1 | 1 | None observed anywhere. |
| Maturing of seedtime rating, 1 earliest | 5.4 | 4.5 | 5.5 | 4.8 | Medium late. |
| Quality of seed rating 1 most | 5.7 | 4.2 | 3.8 | 4.4 | About average. |
| Seedhead height, inches | 14.2 | 14.5 | 19.3 | 15.2 | In lower 50%. |

NOTE.—Ratings range: 1 most desired; 3 is good; 5 is average; 9 least desired.

AQ6 has excellent dark green color and low growth, has excellent resistance to stem rust and produces heavy seed; and has better disease resistance in some categories, as well as being more productive of seed.

Many distinctive characteristics of AQ6 as respects most other bluegrasses are similar to Dwarf, and except where noted otherwise in the foregoing table, it may be assumed that the distinctions of Dwarf as respects other bluegrasses are similar for AQ6.

I claim:

1. A new and distinct variety of bluegrass plant, substantially as described and illustrated and particularly characterized by excellent stem rust resistance, in addition to low and slow growth habit and dark green color.

No references cited.

ROBERT E. BAGWILL, Primary Examiner